United States Patent [19]

Rasmussen

[11] Patent Number: 5,169,106

[45] Date of Patent: Dec. 8, 1992

[54] QUICK ATTACH/RELEASE POLE CLAMP

[75] Inventor: Edward G. Rasmussen, Carrollton, Tex.

[73] Assignee: McGaw, Inc., Irvine, Calif.

[21] Appl. No.: 693,924

[22] Filed: Apr. 29, 1991

[51] Int. Cl.⁵ ............................................. A47B 96/06
[52] U.S. Cl. ................................. 248/230; 248/231.3; 248/231.4
[58] Field of Search ............... 248/230, 231.3, 231.4, 248/316.2, 316.3, 316.4, 218.4; 403/374, 409.1, 110

[56] References Cited

U.S. PATENT DOCUMENTS

| 809,448 | 1/1906 | Kahn | 248/231.3 X |
| 1,760,346 | 5/1930 | Correa | 248/231.4 X |
| 1,842,545 | 1/1932 | Glantz | 248/230 |
| 3,672,619 | 6/1972 | Bowen | 248/316.3 X |
| 4,134,499 | 1/1979 | Joswig | 248/316.3 X |
| 4,674,722 | 6/1987 | Danby et al. | 248/231.3 |

FOREIGN PATENT DOCUMENTS

| 216890 | 1/1942 | Switzerland | 248/231.3 |
| 226940 | 1/1925 | United Kingdom | 248/230 |

Primary Examiner—Carl D. Friedman
Assistant Examiner—Derek J. Berger
Attorney, Agent, or Firm—Ross, Howison, Clapp & Korn

[57] ABSTRACT

A quick attach/release pole clamp is mounted on the side of a medical instrument case. A stationary clamp member is secured to the case and a movable clamp member slides in a slot oriented at a slight acute angle to the vertical, so that it moves toward and away from the stationary clamp member as it moves up and down the slot. A spring biases the movable clamp member toward the top of the slot so that the clamp is moved to the closed position. The user may support the instrument case in two hands while depressing the sliding clamp member to permit the clamp members to be positioned around a pole. When the pressure is released, the spring causes the clamp to close on the pole. A camming lever permits the user to provide positive latching of the clamp member from movement, and to engage an anti-rotation element with the pole. An interlock prohibits activation of the camming lever while the movable clamp member is being depressed.

11 Claims, 5 Drawing Sheets

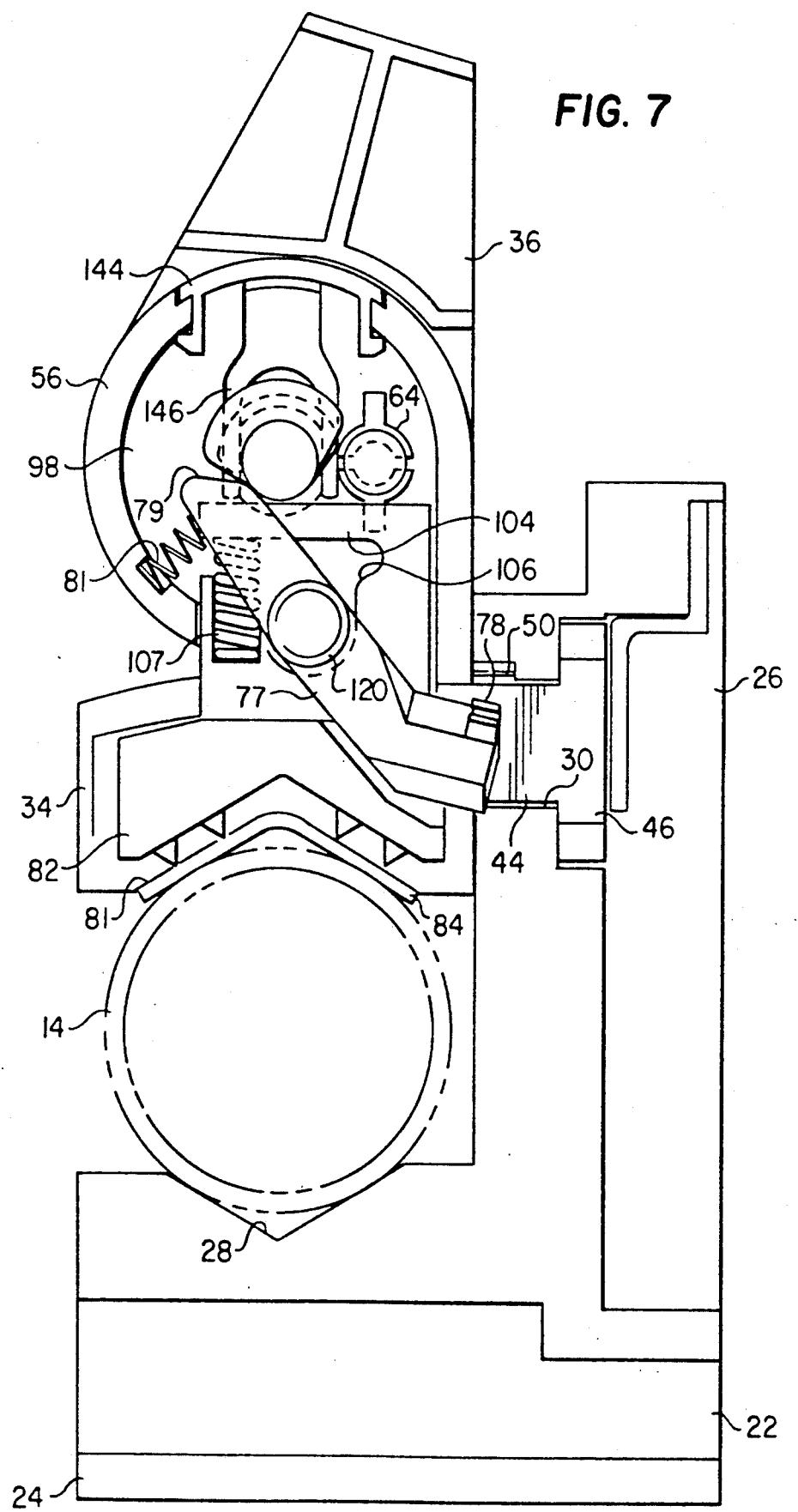

QUICK ATTACH/RELEASE POLE CLAMP

FIELD OF THE INVENTION

This invention relates to a clamp for securing a medical instrument to a pole, and more particularly to such a pole clamp which may be easily engaged and disengaged.

BACKGROUND OF THE INVENTION

In the hospital environment, it is often necessary to provide medical instrumentation at the patient bedside. Many surgical patients, for example, are provided at least on a temporary basis with an intravenous fluid delivery setup for infusion of fluids to prevent dehydration, to preserve electrolyte balance, or to deliver antibiotics and other medication. Frequently, intravenous delivery is provided by a fluid infusion pump or a gravity controller, both of which are electro-mechanical instrumentation which must be situated near the patient.

Typically, the instrument cases of these and other instrumentation used in patient care are provided with clamps for engaging a portable pole so that the instrumentation may be secured on such a pole. The typical pole clamp is located on the back of the instrument case, and is activated by turning a threaded clamping member to close the clamp on the pole. To carry out this securement step, the nurse or other user must support the instrument case with one hand, while turning the clamp knob with the other hand to effect closure. Removal of the instrument likewise requires that the instrument be supported by one hand during the step of unscrewing the clamping knob to free the instrument from the pole. While such clamping arrangements have been in use for many years, they can be awkward and time-consuming to utilize. The present invention provides a pole clamp for use on such instrumentation which may be much more easily and quickly engaged and disengaged.

SUMMARY OF THE INVENTION

In accordance with the invention, there is provided an instrument case carrying a first clamping member. A second clamping member is positioned confronting the first clamping member. Biasing means are provided which urge the second clamping member toward engagement with the first clamping member. An actuator adapted to being depressed by a single digit of a hand holding the case is provided which, when depressed, causes relative movement of the two clamping members apart to permit their placement around a pole. When the actuator is released, the biasing means causes the second clamping member to be urged toward the first, creating a gripping action on the pole. Thus the clamp is engaged simply by the depression and release of the clamp actuator.

In the preferred embodiment, the second clamping member is guided along a slot oriented at an acute angle to the vertical. In a specific form of the invention, a positive latch may be engaged by the user to prevent movement of the second clamping member after the pole clamp is engaged. An interlock is also provided to prevent actuation of this latch at times when the clamp actuator is depressed to open the clamp. In a specific device, the second clamping member can be provided with an anti-rotation element which may be engaged to prevent rotation of the instrument case on the pole after clamp closure. The positive latch and anti-rotation element may be activated by a single camming lever the rotation of which sequentially effects the latching and then the anti-rotation activation.

In the preferred embodiment, the clamp is opened by depressing the top surface of the camming lever to move the sliding clamp member and open the clamp. Thus, the top surface of the camming lever serves as the actuator to be pressed by the user. Preferably, the first movement of the top lever surface in this embodiment causes the interlock to engage so that the positive latch cannot be activated as long as the actuator is depressed.

BRIEF DESCRIPTION OF THE DRAWINGS

For a more complete understanding of the present invention and for further advantages thereof, reference is now made to the following Description of the Preferred Embodiments taken in conjunction with the accompanying Drawings in which:

FIG. 7 is a horizontal cross-section of the clamp slide and associated camming mechanism.

DESCRIPTION OF THE PREFERRED EMBODIMENT

Figure 1:
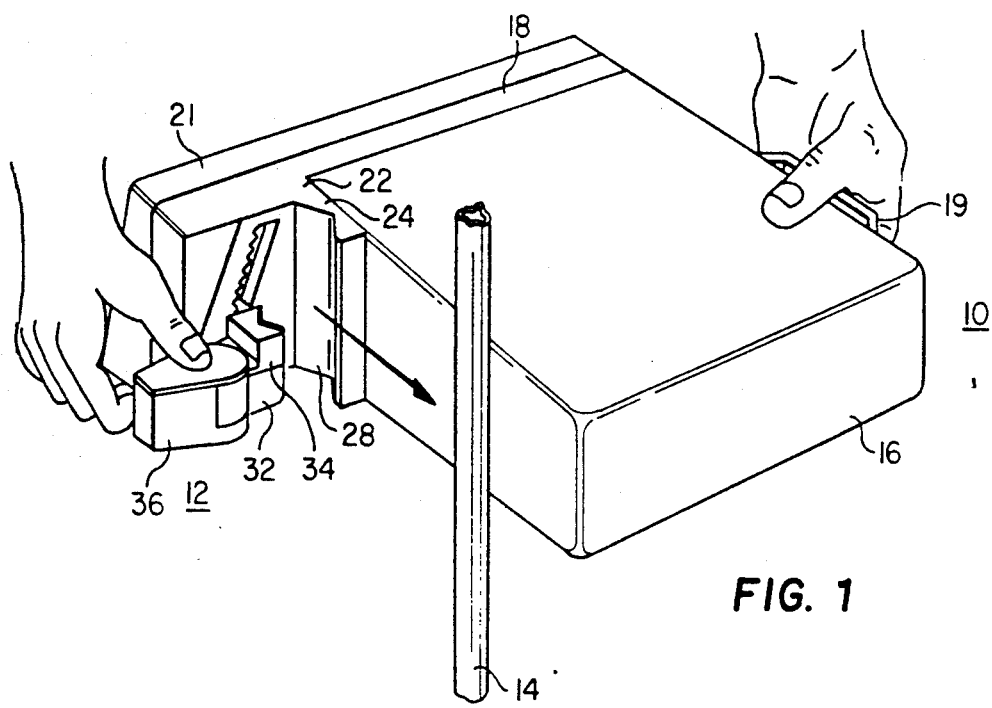
FIG. 1 is a perspective view of a medical instrument case with pole clamp constructed in accordance with a preferred embodiment of the invention, with the clamp opened in preparation for placement about a pole.
Figure 2:
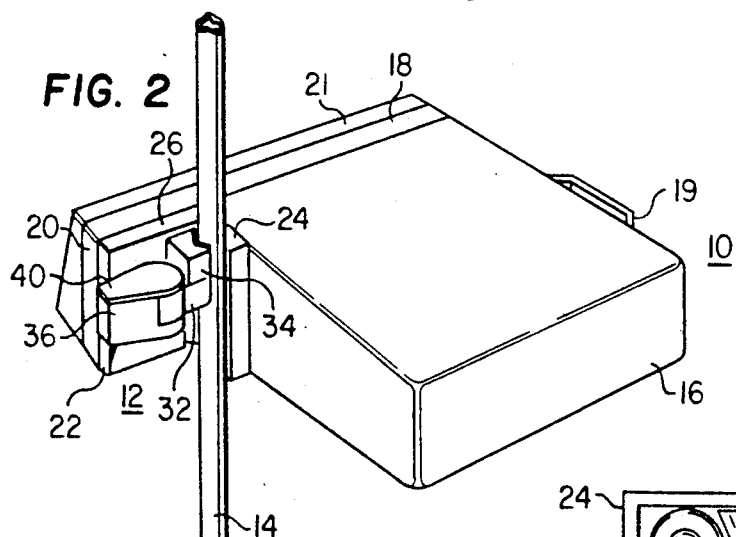
FIG. 2 is a view similar to FIG. 1, with the clamp engaging the pole.
Figure 3:
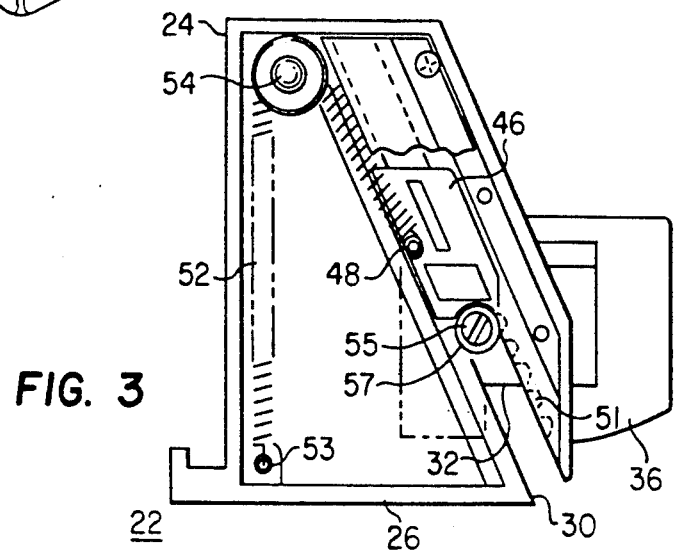
FIG. 3 is a front elevation of the clamp, with the case removed for illustration.
Figure 4:
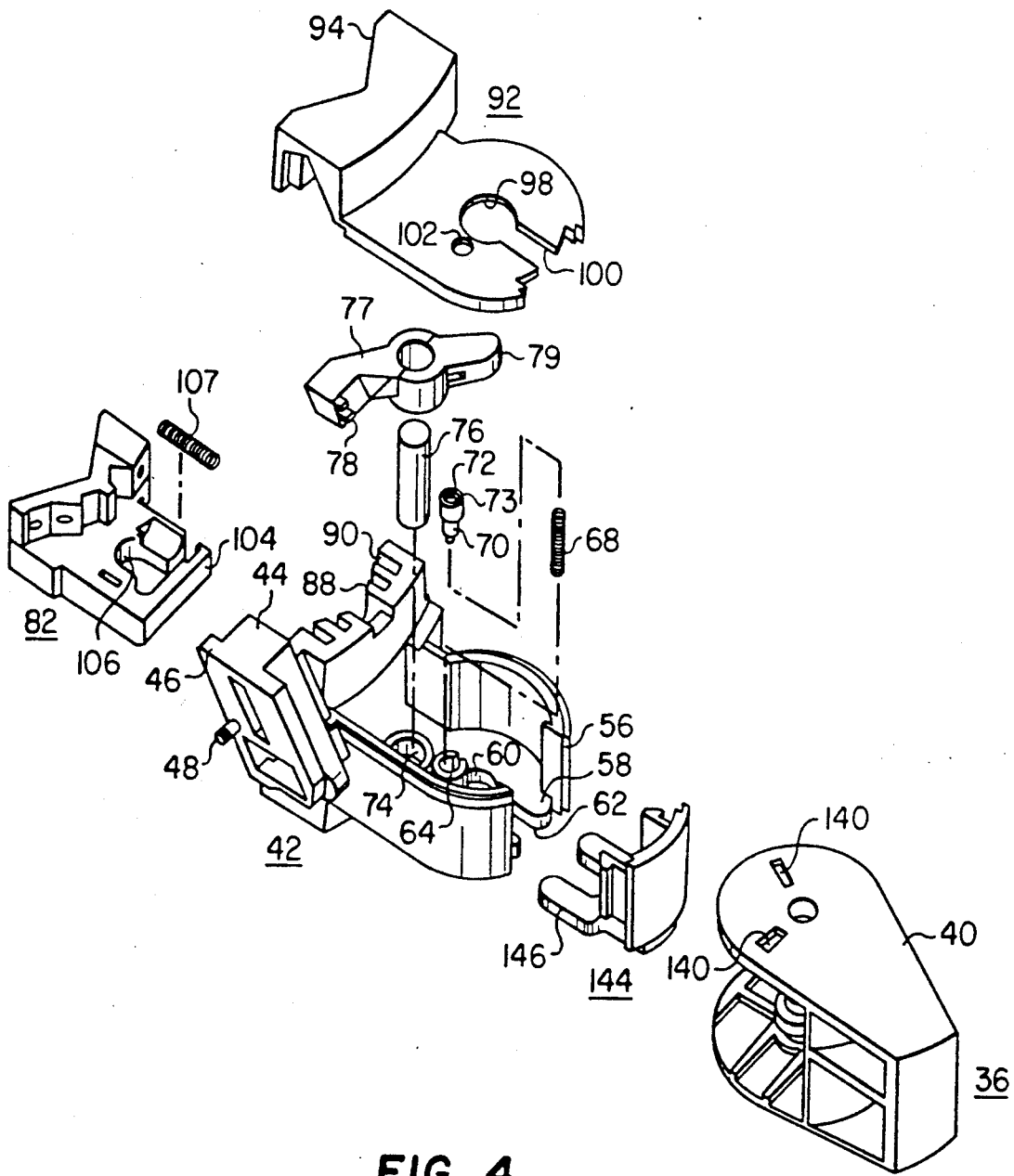
FIG. 4 is an exploded perspective view showing the components of the clamp slide and associated camming mechanism.
Figure 5:
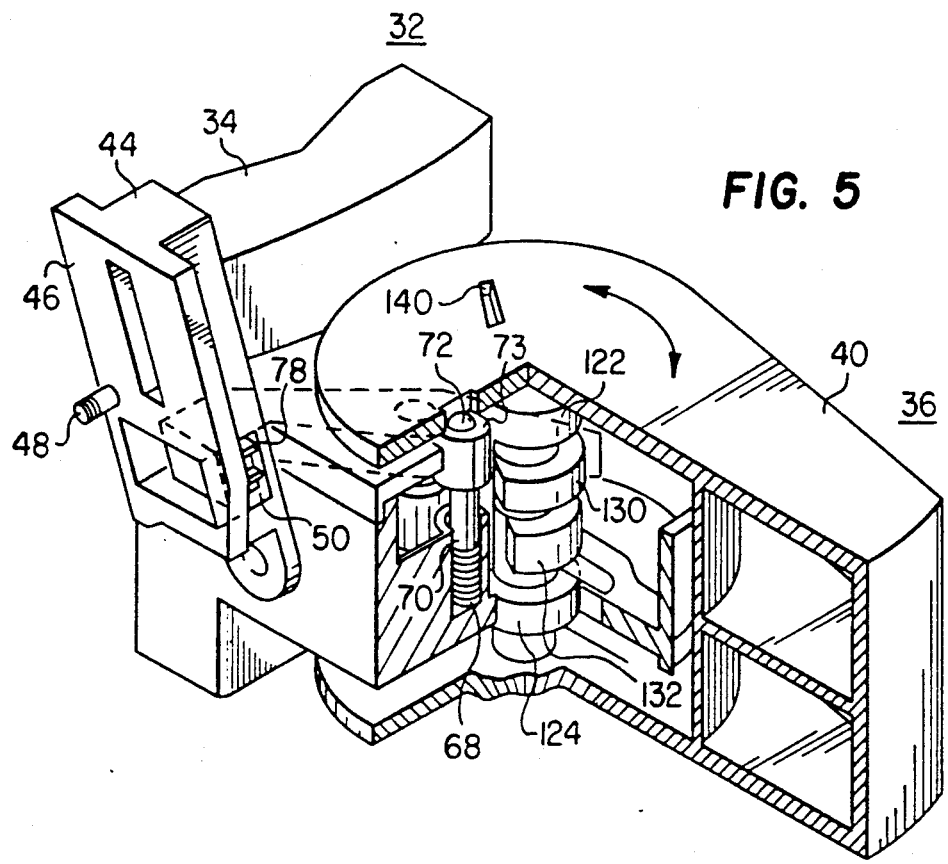
FIG. 5 is a perspective view, partially cutaway, showing the clamp slide and associated camming mechanism.
Figure 6:
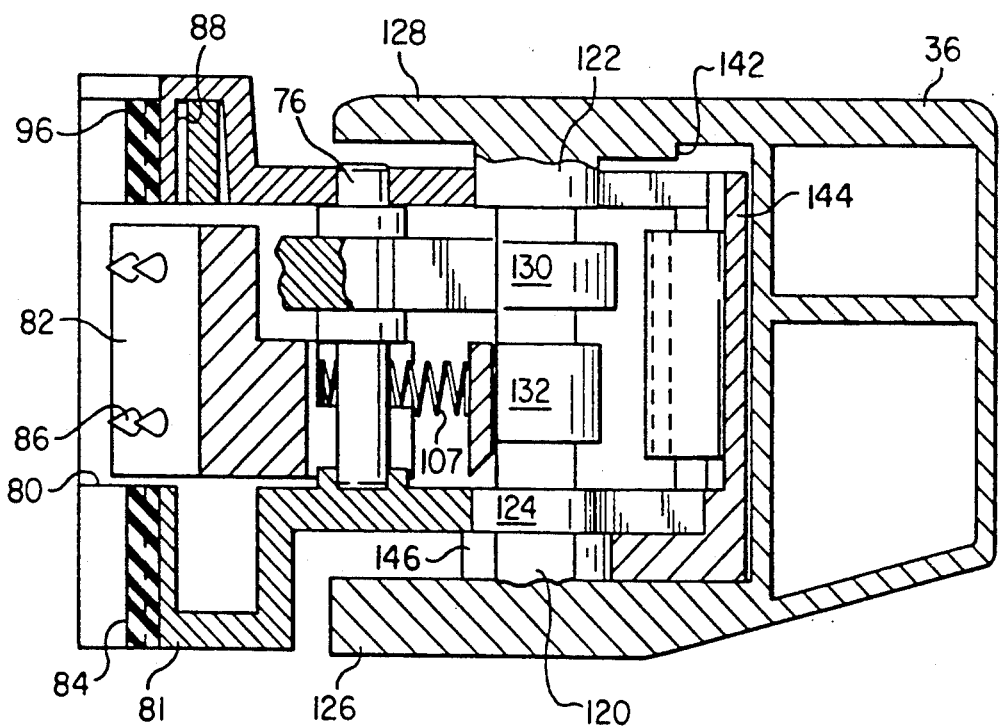
FIG. 6 is a vertical cross-section of the clamp slide and associated camming mechanism.

An instrument case 10 with a quick attach/release pole clamp 12 constructed in accordance with the present invention is illustrated in overview by FIGS. 1 and 2. Instrument case 10 may house any of the medical instrumentation typically utilized in the hospital environment. For example, instrument 10 may be an intravenous fluid pump, an intravenous fluid gravity controller, or other instrument which may desirably be placed adjacent a patient bed by securement on a portable pole 14.

Instrument case 10 is provided with a main body portion 16 extending to the rear of the instrument, and a front panel 18. Main body portion 16 carries a handle 19 on its side opposite clamp 12. Main body portion 16 and panel 18 are preferably relatively thin in vertical extent. Front panel 18 extends laterally across the front of main body portion 16, and has a width which is greater than the main body portion 16, so that at least one end 20 of front panel 18 extends laterally beyond the edge of main body portion 16. Door 21 gives access to the front of panel 18. Panel 18 may typically accommodate the mechanical interface for an I.V. set, and door 21 may provide user controls and displays.

Clamp 12 is installed in the space behind front panel 18 and beside main body portion 16 by mechanical attachment of a rigid frame 22 to case 10. Leg 24 of frame 22 extends rearwardly from front panel 18. Leg 24 abuts the side of main case body portion 16 and is mechanically secured thereto. Leg 26 of frame 22 extends parallel to, and is mechanically secured to, front panel 18. Leg 24 is provided with a stationary clamping member 28 in the form of a vertically extending V-shaped recess to receive pole 14. Leg 26 of frame 22 is provided with a guide slot 30 which is oriented at an acute angle with respect to the vertical, so that slot 30 inclines toward main case body 16.

Slide member 32 is positioned to be moved up and down along slot 30. Slide member 32 includes a clamping member 34 confronting stationary clamping member 28. Clamping member 34 moves toward and away from the stationary clamping member 28 as the slide member 32 is guided up and down in slot 30. Slide member 32 is biased to the upper end of slot 30. Slide member 32 also carries a camming lever 36, the details of which will be discussed below.

As shown in FIG. 1, case 10 may be held by a nurse or other user in two hands, and quickly prepared for attachment to receiving pole 14 by merely pressing down on top surface 40 of camming lever 36 with the thumb of the right hand to move slide member 32 down in slot 30 and thus move the V-shaped recess of clamping member 34 away from stationary clamping member 28 so that the clamping members 28 and 34 may be placed on the opposite sides of pole 14. When pressure on surface 40 is removed, slide member 32 moves upwardly in slot 30 so that the pole 14 is gripped between clamping members 28 and 34, holding instrument 10 in position on the pole, as shown in FIG. 2.

The construction of slide member 32 including the camming lever 36 which it carries is illustrated in more detail by FIGS. 3 through 8. The main body of slide member 32 is formed by slide housing base 42. Arm 44 of housing base 42 is dimensioned so that it is slidingly movable in slot 30 on frame 22. Arm 44 is provided at its forward side with mounting flange 46 which is positioned on the front side of slot 30 to retain arm 44 within the slot. Flange 46 carries spring mounting post 48. Latching aperture 50 is formed in the lower end of the side of arm 44. A toothed rail 51 is formed on leg 26 of frame 22 adjacent slot 30, for cooperation with a latch 77 on slide member 32 extendable through aperture 50. Arm 44 is positioned in slot 30 with the flange 46 on the front side of slot 30 by sliding it into the open slot at the bottom of frame 22. A biasing spring 52 is connected at one end to post 53 at the bottom of frame 22, and extends vertically up over pulley 54 and thence is connected to post 48 on flange 46, to exert a biasing force on slide member 32 toward the top of slot 30, in the direction of closure of the clamp 12. Shoulder screw 55 is threaded into slide member 32, so that it extends rearwardly of slot 30, and carries an annular ball bearing 57 which engages a wall of slot 30 to smooth the movement of slide member 32.

Housing base 42 includes sidewall 56 extending upwardly about floor 58. Floor 58 is provided with a central aperture 60 and a slot 62 extending from aperture 60 to the edge of floor 58 at a gap in side wall 56. Floor 58 also carries an interlock well 64 which receives interlock spring 68, atop which is positioned interlock plunger 70, biased upwardly by the spring. The top of interlock plunger 70 is a spherical detent surface 72 surrounded by a flat annular shoulder 73.

Floor 58 of housing base 42 also carries latch post mounting depression 74 in which is journalled latch post 76 which carries latch 77.

A toothed end 78 of latch 77 is shaped to engage toothed rail 51 through aperture 50 on arm 44 to secure slide member 32 against movement. The opposite end 79 of latch 77 is shaped to cooperate with a cam to cause rotation of latch 77. A spring 81 is preferably provided to bias latch 77 to the unlatched position.

The lower portion of housing base 42 is provided with a V-shaped lower clamping surface 81 which is provided with an elastomeric friction pad 84. Immediately above the lower clamping surface 81 is a window 80 which receives anti-rotation element 82. Anti-rotation element 82 has a corresponding V-shaped recess on which are positioned two horizontal rows of metal points 86 for engaging pole 14 when anti-rotation element 82 is pushed forward through window 80. Above anti-rotation element 82 and window 80 is a V-shaped structure 88 on base 42 with grooves 90 formed at the top of slide housing base 42 for mating with complimentary surfaces of slide housing cover 92 which snap fits onto base 42. Housing cover 92 includes a V-shaped clamping surface 94 which also receives an elastomeric friction pad 96 for gripping pole 14. A V-shaped recess is thus provided on movable clamping member 34 by upper clamping surface 94 and lower clamping surface 81, separated by window 80, and each provided with friction pads for gripping pole 14.

A central aperture 98 is formed in the housing cover 92 for journalling camming lever 36, and a slot 100 extends from aperture 98 to the edge of cover 92 for positioning lever 36. Aperture 98 and slot 100 are aligned with aperture 60 and slot 62 on base 42. A detent aperture 102 is also formed in housing cover 92 for receiving interlock plunger 70.

Anti-rotation element 82 includes a laterally extending finger 104 which defines an opening 106 accommodating latch post 76 in the assembled device. Spring 107 is positioned between finger 104 and the body of anti-rotation element 82. The force of spring 107 may be selected for the purpose of adjusting the mechanical linkage between finger 104 and the main body of anti-rotation element 82. By selection of the spring force, one can selectively establish the force to be imparted to gripping points 86 by a controlled movement of finger 104. Slide housing cover 92 also carries a journalling depression (not shown) corresponding to depression 74 for rotatably receiving latch post 76.

When slide housing cover 92 is snap-fit onto slide housing base 42, latch pivot post 76 is rotatably mounted in slide member 32 and carries latching arm 77. Latching arm 77 is spring biased to the unlatched position by spring 81. Interlock plunger 70 is spring loaded upwardly so that its spherical detent surface 72 extends through aperture 102 in housing cover 92. Anti-rotation element 82 is positioned between the V-shaped gripping surfaces 96 and 84, and is slidably movable outwardly from slide member 32 to grip pole 14.

Anti-rotation element 82 and latch arm 77 are operated by camming lever 36 which is mounted on slide member 32. Camming lever 36 includes a central pivot pin 120 which has integrally formed thereon upper bearing surface 122 and lower bearing surface 124. Pivot pin 120 extends between lower lever wall 126 and upper lever wall 128. Pivot pin 120 carries latch camming surface 130 and anti-rotation camming surface 132. Lever 36 is placed into operating position by sliding it around and into slide member 32. With upper lever wall 128 positioned above the top of slide housing cover 92, and lower lever wall 126 positioned below floor 58 of slide housing base 32, the lever pivot pin 120 is moved along slots 62 and 100 until positioned at mounting apertures 60 and 98. At that point, lever 36 is dropped so that bearing surface 122 is journalled in aperture 98 and bearing surface 124 is journalled in aperture 60. Lever 36 is thus rotatable with respect to slide member 32. Camming surface 130 is positioned adjacent end 79 of latching arm 77, while camming surface 132 is positioned adjacent finger 104 of anti-rotation element 82. Upper wall 128 of lever 36 is provided with detent slots 140 for receiving spherical detent 72 to define the fully locked and fully open positions of lever 36.

The upper wall 128 of lever 36 is also provided on its bottom surface with a narrow interlock rib 142 which is positioned adjacent slot 100 in slide housing cover 92. With no manual pressure on the upper surface 40 of lever wall 128, the interlock spring 68 causes shoulder 73 of plunger 70 to hold upper lever wall 128 above the top of housing cover 92. In this position interlock rib 142 is clear of slot 100, so that it does not interfere with rotation of lever 36. When manual pressure is applied to depress lever 36, upper wall 128 initially acts to compress spring 68 and thus move wall 128 against housing cover 92. This initial movement causes rib 142 to move into slot 100, preventing rotation of lever 36 while the clamp is opened. After the lever 36 has been assembled in the device, the opening in side wall 56 of slide housing base 42 may be closed by closure member 144 snap fit onto base 42. Closure member 144 includes feet 146 which extend inwardly along floor 58 of base 42 to surround lever pivot pin 120 and hold it down in its position in slide member 32 by overlying the aperture 60 and bearing surface 124.

Use of the assembled device is readily understood, and simply and quickly carried out. With the camming lever 36 in the unengaged position illustrated in FIGS. 1, 2 and 8A, the clamp 12 may be easily opened to prepare for attachment of the case 10 to the pole 14. The user holds the case in two hands as shown in FIG. 1 and uses his right thumb to apply pressure to activator surface 40 on lever 36, depressing slide member 32, and opening the clamp. After placing clamp members 28 and 34 on opposite sides of pole 14, the clamp is engaged by removing the thumb from lever 36. Spring 52 causes slide member 32 to move up and engage friction pads 84 and 96 with pole 14. The combined effect of spring 52, the weight of instrument 10 and the placement of clamp 12 cooperate to secure case 10 firmly on pole 14. This condition, as depicted in FIG. 2, is sufficient to effect placement of the instrument on the pole, even without rotation of camming lever 36 to engage latch 77 and anti-rotation element 82. However, the case is free to rotate on the pole, which may not be desired, and the clamp is subject to movement of slide member 32 in the event, for example, of a sudden upward impact on the bottom of case 10.

Figure 8A:
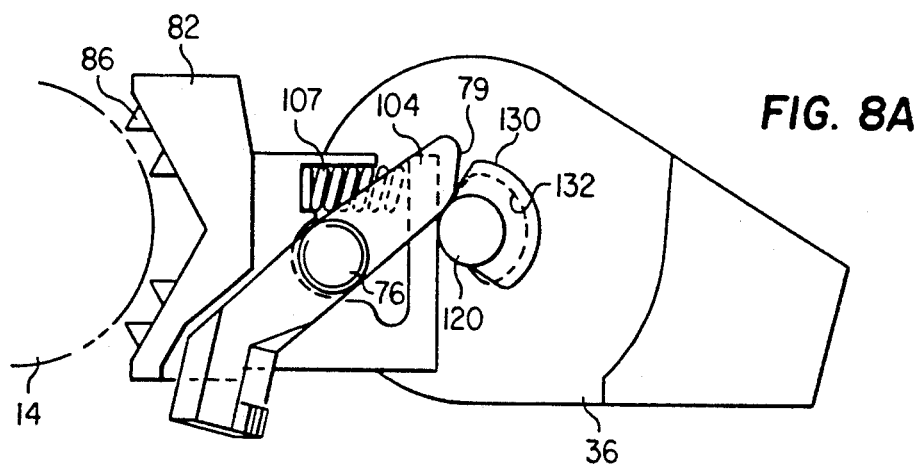
FIGS. 8A, 8B and 8C schematically illustrate three stages of the camming action of the clamp to engage the clamp movement prevention latch and the anti-rotation element.
Figure 8B:
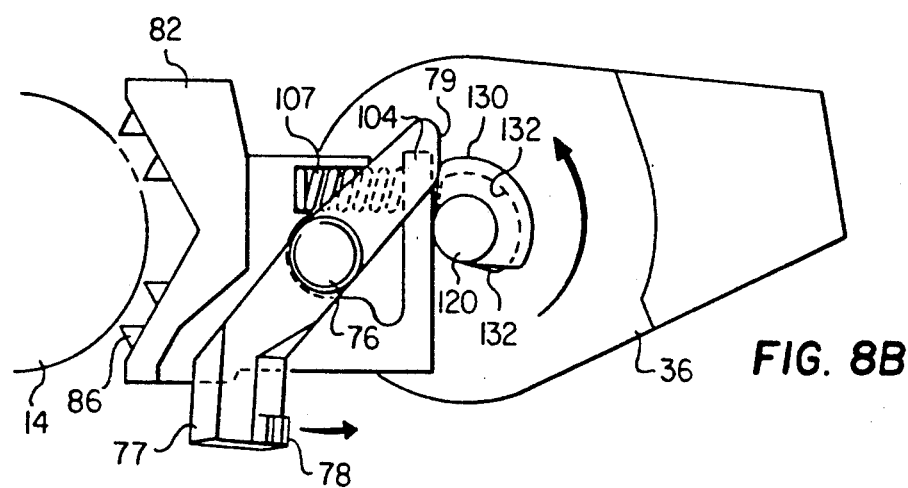
Figure 8C:
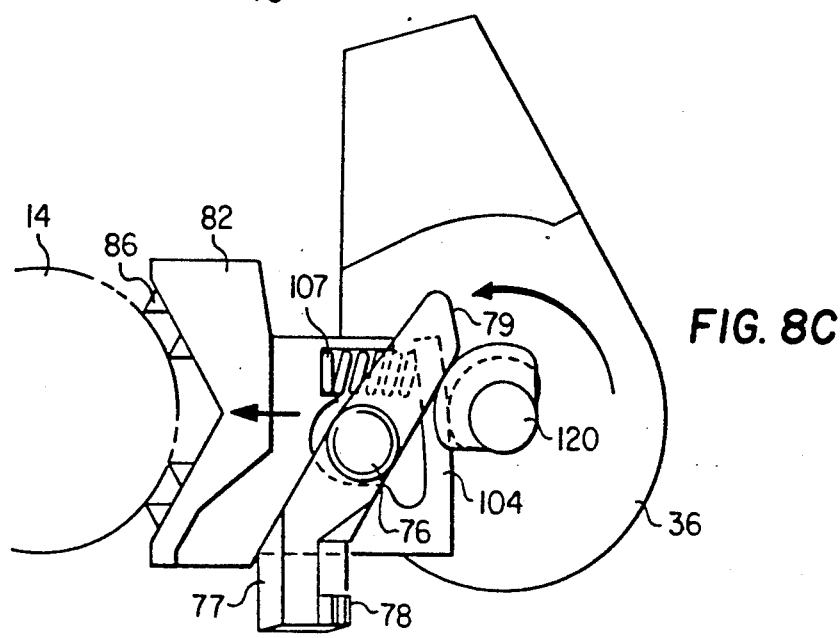

Accordingly, in most instances the user will want to move the clamp to fully protect against clamp release and rotation by rotating lever 36 approximately 120° counterclockwise in a one step securement procedure. This results in the engagement of latch 77 and anti-rotation element 82 as depicted in FIG. 8C. FIG. 8B illustrates an intermediate stage of camming lever 36. At this stage of rotation cam 130 has just begun engagement with latch 77 to initiate its rotation. Cam 132 has not yet begun moving finger 104 to compress spring 107. After the latch 77 is seated in rail 51, cam 132 engages finger 104 to move anti-rotation element points 86 into engagement with pole 14 as shown in FIG. 8C.

Whereas the present invention has been described with respect to a specific embodiment thereof, it will be understood that various changes and modifications will be suggested to one skilled in the art and it is intended to encompass such changes and modifications as fall within the scope of the appended claims.

I claim:

1. A medical instrument mountable on a vertical pole comprising:
   (a) a case adapted to being held by two hands;
   (b) a first clamping member carried by the case;
   (c) a second clamping member confronting the first clamping member;
   (d) biasing means urging the first and second clamping members together to permit gripping of a pole therebetween;
   (e) an actuator adapted to being pressed by a single digit of a hand holding the case to overcome the biasing means and cause relative movement of the first and second clamping members apart to permit their placement about a pole, whereby the instrument may be mounted on a pole by carrying it to the pole with the actuator depressed by the carrier's digit to permit placement of the clamping members around the pole, and by then releasing the actuator to permit the biasing means to cause engagement of the clamping members with the pole;
   (f) a movable slide carrying the second clamping member in a slot guiding the slide at an acute angle to the vertical; and
   (g) a latch actuable to positively prevent movement of the slide.

2. The device of claim 1, further comprising an interlock means for preventing actuation of the latch at times when the actuator is being pressed by the user.

3. The device of claim 2, further comprising an anti-rotation element which is movable to engage the pole after release of the actuator to secure the instrument from rotation on the pole.

4. A pole clamp for an instrument case comprising:
   (a) a first clamping member fixedly mounted to the case;
   (b) a movable slide carrying a second clamping member confronting the first clamping member;
   (c) biasing means urging the first and second clamping members together to permit gripping of a pole therebetween;
   (d) a track guiding the slide at an acute angle to the vertical;
   (e) a toothed rail parallel to the track; and
   (f) an actuator adapted to being pressed to overcome the biasing means and cause relative movement of the first and second clamping members apart to permit their placement about a pole, and carrying a latch for optionally engaging the toothed rail to prevent movement of the slide, whereby the instrument case may be mounted on a pole by carrying it to the pole with the actuator engaged to permit placement of the clamping members around the pole, and then by releasing the actuator to permit the biasing means to cause engagement of the clamping members with the pole.

5. The device of claim 4, further comprising an interlock means for preventing engagement of the latch at times when the actuator is being pressed by the user.

6. The device of claim 5, further comprising an anti-rotation slide associated with the second clamping member which is movable to engage the pole after release of the actuator to secure the instrument from rotation on the pole.

7. The device of claim 6, wherein actuation of the latch and the anti-rotation slide are both affected by rotation of a single lever.

8. The device of claim 7, wherein the lever carries a first cam for actuating the latch and a second cam for actuating the anti-rotation slide after the engagement of the latch with the toothed rail.

9. A medical instrument mountable on a vertical pole comprising:
   (a) a case adapted to being held by two hands;
   (b) a first clamping member carried by side of the case;
   (c) a second clamping member movably confronting the first clamping member;
   (d) biasing means urging the first and second clamping members together to permit gripping of a pole therebetween;
   (e) an actuator adapted to being pressed to overcome the biasing means and cause relative movement of the first and second clamping members apart to permit their placement about a pole, whereby the instrument may be mounted on a pole by carrying it to the pole with the actuator depressed by the carrier's digit to permit placement of the clamping members around the pole, and by then releasing the actuator to permit the biasing means to cause engagement of the clamping members with the pole;
   (f) camming means associated with the actuator rotatable only when the actuator is not being pressed to positively prevent movement of the second clamping member; and
   (g) interlock means preventing rotation of the camming means at times that the actuator is being pressed.

10. The device of claim 9 further comprising a movable slide carrying the second clamping member and a slot guiding the slide at an acute angle to the vertical.

11. The device of claim 9, further comprising an anti-rotation element which is movable by rotation of the camming means.

* * * * *